United States Patent [19]

Hohenlohe-Oehringen et al.

[11] 4,322,360

[45] Mar. 30, 1982

[54] PROCESS FOR PRODUCING IMIDAZOLIDONE INTERMEDIATES OF BIOTIN

[75] Inventors: Kraft Hohenlohe-Oehringen, Innsbruck, Austria; Anton Fliri, Cambridge, Mass.

[73] Assignee: Hoffmann-La Roche Inc., Nutley, N.J.

[21] Appl. No.: 246,839

[22] Filed: Mar. 23, 1981

Related U.S. Application Data

[62] Division of Ser. No. 135,796, Mar. 31, 1980, Pat. No. 4,284,788.

[30] Foreign Application Priority Data

Apr. 6, 1979 [CH] Switzerland ............... 3293/79

[51] Int. Cl.$^3$ .................................. C07C 117/02
[52] U.S. Cl. ................................................ 260/349
[58] Field of Search .......................... 260/349, 345.2

[56] References Cited

U.S. PATENT DOCUMENTS 2,912,391 11/1959 Hardy et al. .................. 260/349
3,859,261 1/1975 Breslow ....................... 260/349
4,044,020 8/1977 Marx et al. .

FOREIGN PATENT DOCUMENTS 2508831 9/1975 Fed. Rep. of Germany .

OTHER PUBLICATIONS

Barton, J., in Protective Groups in Organic Chemistry (McOmie, Editor), Plenum Press, London, pp. 43–83 (1973).
Bestian, H., Pure Appl. Chem, 27, 611 (1971).
Borowitz, et al., J. Org. Chem, 31, 3032–3037 (1966).
Eliel, et al., Conformational Analysis, Interscience, New York, pp. 189–255 (1965).
Graf, R., Liebigs Ann Chem., 661, 111 (1963).
Isaka, et al., Chemical Abstracts, 69:27175x (1968).
Kempter, et al., Chemical Abstracts, 76:9957r (1972).
Matsui, M., Preparation of Active Biotins, Patent Abstracts of Japan, Band 2, No. 110 for Kokai No. 53-73588 (Sep. 13, 1978).
Matsui, M., Preparation of Active Biotins, Patent Abstract of Japan for Kokai No. 53-73589 (Sep. 13, 1978).
Moriconi, E., Mechanism of Reactions of Sulfur Compounds, vol. 3, Intrascience Rsch. Foundation, Santa Maria, Cal., pp. 131–140 (1968).
Ogawa, et al., Carbohydrate Research, 57, C31–C35, (1977).
Ohrui, et al., Tett. Lett., 2765–2766 (1975).

*Primary Examiner*—Ethel G. Love
*Attorney, Agent, or Firm*—Jon S. Saxe; Bernard S. Leon; George W. Johnston

[57] ABSTRACT

A process is disclosed for producing imidazolidone intermediates from 2H-chromene. The intermediates are useful for synthesizing biotin.

1 Claim, No Drawings

PROCESS FOR PRODUCING IMIDAZOLIDONE INTERMEDIATES OF BIOTIN

This is a division of application Ser. No. 135,796 filed Mar. 31, 1980, now U.S. Pat. No. 4,284,788.

SUMMARY OF THE INVENTION

The invention concerns a process for producing imidazolidone intermediates useful in the synthesis of biotin.

In the process of the invention, 2H-cumene is converted via various intermediates to a compound of the formula:

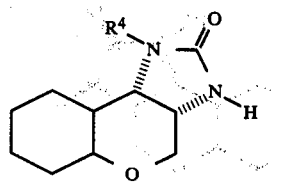

wherein $R^4$ is hydrogen.

Compound I then is converted into its alkali metal salt, preferably its lithium salt, and selectively reduced to a compound of the formula:

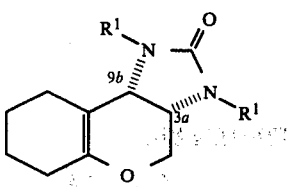

wherein $R^1$ is hydrogen.

Compound II then is oxidized to a compound of the formula:

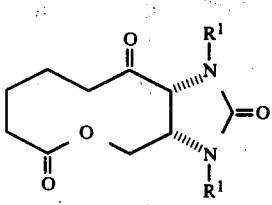

wherein $R^1$ is as above.

Compound III then is reduced to a compound of the formula:

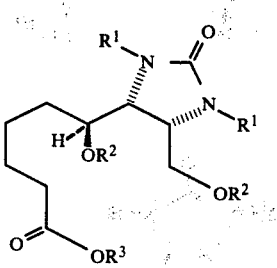

wherein $R^1$ is as above, $R^2$ is hydrogen; and $R^3$ is lower alkyl or aralkyl, which in turn is converted to a compound of the formula:

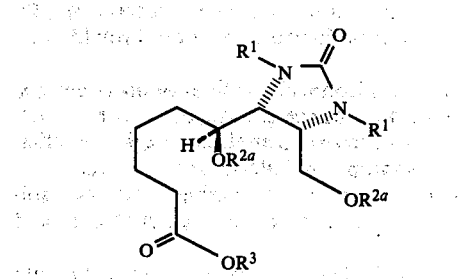

wherein $R^1$ and $R^3$ are as above and $R^{2a}$ is organosulphonyl.

Compound IVa is treated with a sulphide to form a biotin ester of the formula:

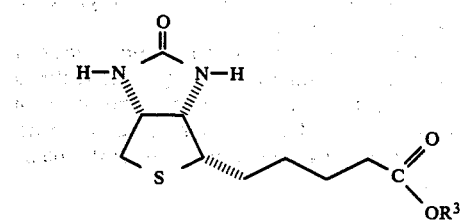

wherein $R^3$ is as above, which then is hydrolyzed to biotin of the formula:

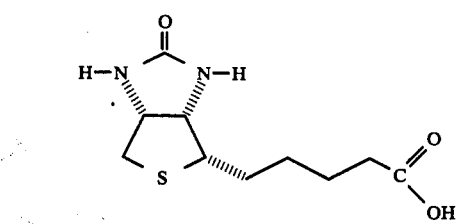

If desired either compound II, III or IV wherein $R^1$ is hydrogen can be converted to a corresponding compound wherein $R^1$ is a nitrogen protecting group.

DETAILED DESCRIPTION OF THE INVENTION

The invention relates to a process for manufacturing imidazolidone derivatives which are suitable as intermediates for producing biotin. The invention also concerns novel intermediates in this process.

As used herein, alkyl connotes straight or branched chain saturated aliphatic hydrocarbon groups of 1 to 20 carbon atoms. Lower alkyl denotes alkyl groups of 1 to 6 carbon atoms, such as methyl, ethyl, propyl, isopropyl, butyl and like. Methyl is preferred.

Aryl denotes mononuclear aromatic hydrocarbon groups such as phenyl and the like which can be unsubstituted or substituted in one or more positions with halogen, nitro, lower alkylenedioxy, lower alkyl or lower alkoxy. Aryl also denotes polynuclear aromatic groups such as napthyl, anthryl, phenanthryl, azulyl and the like which can be unsubstituted or substituted with one or more of the aforementioned substituents.

Aralkyl connotes a group comprising aryl and alkyl moieties as defined hereinbefore. Examples are benzyl and alpha-lower alkyl substituted benzyls (e.g., cumyl).

Alkali metals include lithium, sodium, potassium and rubidium. Alkaline earth metals include barium, magnesium, calcium and strontium.

Halogen denotes fluorine, chlorine, bromine and iodine. Halide connotes fluoride, chloride, bromide and iodide.

Alkanol denotes alcohol derivatives of alkyl groups. Lower alkanols are alkanol groups of 1 to 6 carbon atoms. Examples of lower alkanols are methanol, ethanol, propanol, isopropanol, butanol and the like.

Aralkanols denote alcohol derivatives of aralkyl moieties. Examples are benzyl alcohol, cumyl alcohol and the like.

Organosulphonyl denotes lower alkyl sulphonyl groups, arylsulphonyl groups and aralkylsulphonyl groups. Examples are methanesulphonyl, toluenesulphonyl and benzenesulphonyl.

Nitrogen protecting groups are conventional nitrogen protecting moieties utilized in biotin chemistry. Examples are aralkyl (e.g., benzyl), allyl (i.e., —CH$_2$CH=CH$_2$) and the like.

In the pictorial representations of the compounds of this application, a solid tapering line (▬) indicates a substituent in the beta-orientation (above the plane of the molecule) and a dashed line (- - -) indicates a substituent which is in the alpha-orientation (below the plane of the molecule).

In accordance with one aspect of the invention, biotin of the formula:

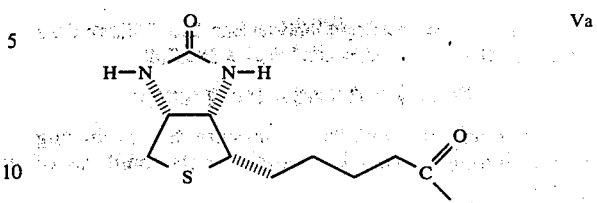

is produced from a compound of the formula:

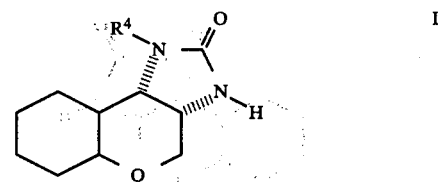

wherein R$^4$ is hydrogen,
by the following reaction scheme:

REACTION SCHEME 1

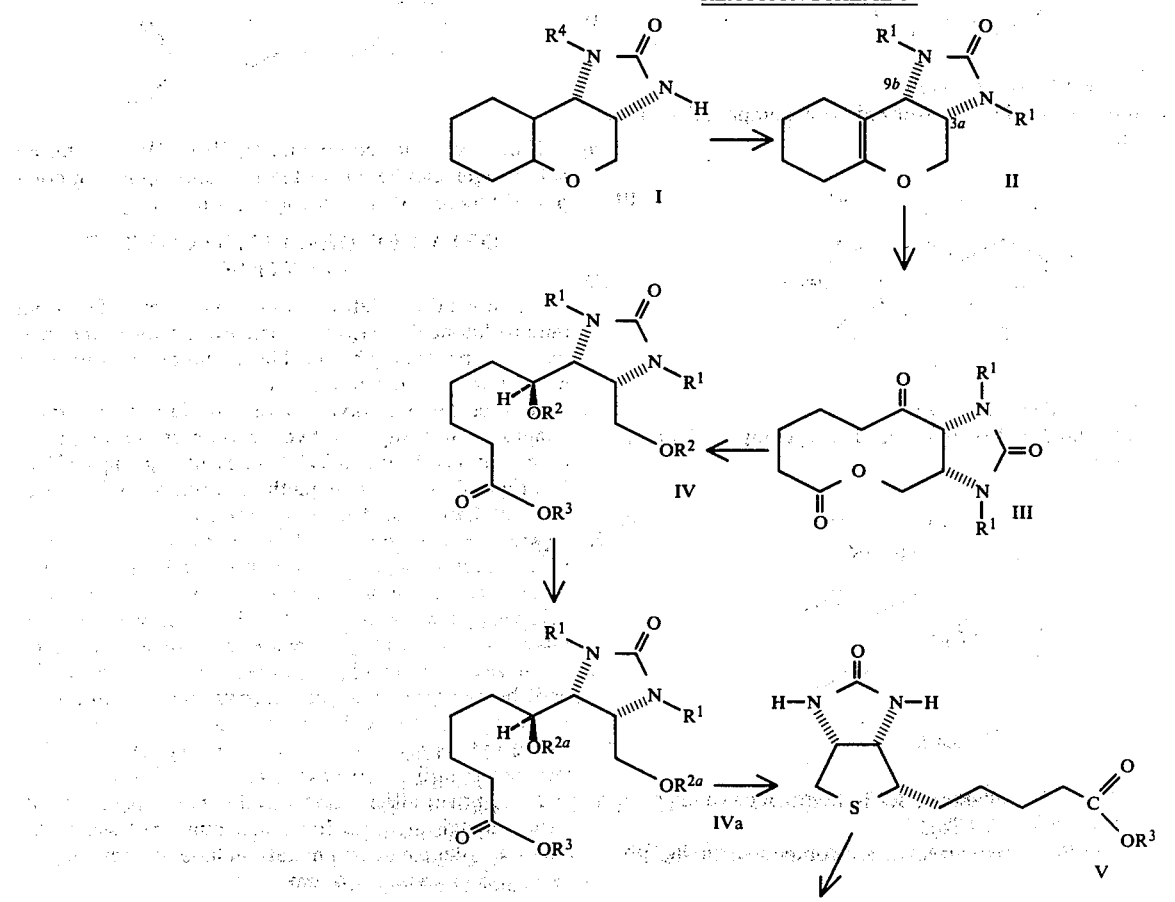

REACTION SCHEME 1

-continued

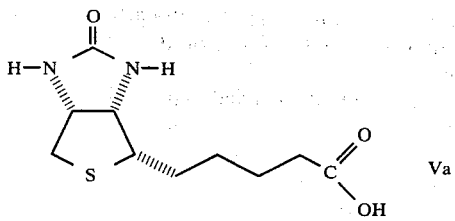

wherein
$R^1$ is hydrogen or a nitrogen protecting group;
$R^2$ and $R^4$ each are hydrogen; $R^{2a}$ is organosulphonyl; and
$R^3$ is lower alkyl or aralkyl.

In accordance with Reaction Scheme 1, compound I is reduced to compound II via a corresponding alkali metal salt of compound I.

Compound I is converted into its alkali metal salt such as its lithium salt, by any conventional technique for forming alkali metal salts from its corresponding amidazolidones. For example, compound I is reacted with an amide (e.g., lithium diisopropylamide) in a lower alkylamine solvent (e.g., ethylamine) to yield the desired salt. Although not critical, the reaction temperature generally is chosen according to the boiling point of the amine solvent.

As a further illustration, compound I is converted to its alkali metal salt, such as its potassium salt, by treatment with potassium tert.butoxide.

The alkali metal salt of compound I is then converted to compound II in a one step or a two step reduction process.

The one step reduction of compound I to compound II conveniently is carried out using lithium in a lower alkylamine solvent such as a monoalkylamine or a dialkylamine. Ethylamine, dimethylamine or their mixtures are preferred solvents. The one step reduction is conveniently carried out while heating at reflux (i.e., at the boiling point of the amine). Reaction times of several hours (e.g., 14 hours) are required.

The first step in the two-step reduction of compound I to compound II is carried out using lithium in liquid ammonia thus obtaining the corresponding octahydro compound of compound I. In the second step, the octahydro compound is catalytically hydrogenated to give decahydro compound II wherein $R^1$ is hydrogen.

Compound II is then oxidized to compound III by any conventional oxidizing technique.

The oxidation of compound II to compound III can be carried out in one or two steps.

Illustratively, a one step (direct) oxidation of compound II to compound III can be carried out using chromic acid in acetone as the oxidating agent.

The direct oxidation can also be carried out using an organic peracid (e.g., peracetic acid, perbenzoic acid, a halogenated perbenzoic acid such as m-chloroperbenzoic acid, trifluoromethylperbenzoic acid or monoperphthalic acid). Such peracids preferably are used in amounts of several equivalents.

The direct oxidation of compound II to compound III can also be carried out using an appropriate oxide such as ruthenium dioxide.

In the two-step oxidation of compound II to compound III, firstly compound II is oxidized to its corresponding dihydroxy compound and secondly this dihydroxy compound is oxidized to compound III.

Illustratively, the first step of this two-step oxidation is carried out with a peracid (e.g., peracetic acid, perbenzoic acid, a halogenated perbenzoic acid such as m-chloroperbenzoic acid, trifluoromethylperbenzoic acid or monoperphthalic acid). The peracid preferably is used in equivalent amounts.

The second step of the two-step oxidation is carried out using sodium periodate. Instead of sodium periodate, lead tetraacetate can also be used as the oxidizing agent. If desired, the dihydroxy compound formed in the first oxidation step need not be isolated.

Compound III is then selectively reduced to compound IV.

The reduction of a compound III to compound IV can be carried out using a metal borohydride such as an alkali metal borohydride (e.g., sodium borohydride, potassium borohydride or lithium borohydride) or using zinc borohydride. Sodium borohydride is the preferred reducing agent.

The reduction of compound III to compound IV preferably is carried out in the presence of an organic solvent which is capable of bringing about an ester formation (i.e., substitutent $R^3$ of compound IV is lower alkyl or aralkyl, preferably benzyl). Suitable solvents are lower alkanol or aralkanol. Methanol and benzyl alcohol are preferred solvents.

Although temperature is not critical, the reduction can be carried out at room temperature (about 23° C.) or at somewhat elevated temperatures (about 23° C. to about 50° C.). Elevated temperatures are convenient when zinc borohydride is used as the reducing agent.

If desired, $R^1$ of either compound II, III or IV can be converted from hydrogen to a nitrogen protecting group. Any known manner for adding nitrogen protecting groups onto imidazolidones can be utilized. For example, compound II, III or IV wherein $R^1$ is hydrogen can be reacted with an aralkyl halide (e.g., benzyl chloride) or an allyl halide to form corresponding compounds wherein $R^1$ is a nitrogen protecting group.

In accordance with the above procedure, Compound II wherein $R^1$ is a nitrogen protecting group then can be oxidized to compound III wherein $R^1$ is a nitrogen protecting group which in turn can be reduced to compound IV wherein $R^1$ is a nitrogen protecting group.

Compound IV wherein $R^1$ is hydrogen or a nitrogen protecting group and $R^2$ is hydrogen is converted to compound IVa wherein $R^1$ is as above and $R^{2a}$ is organosulphonyl. This conversion can be carried out by reacting compound IV with a suitable sulphonic acid halide (e.g., methanesulphonyl chloride, toluenesulphonyl chloride or benzenesulphonyl chloride). A tertiary amine base (e.g., pyridine and triethylamine) preferably is used as the solvent in this reaction. Although temperature is not critical, the reaction is generally carried out at a temperature between about −10° C. and about room temperature (about 23° C.).

Compound IVa then is converted into biotin ester V by treatment with a sulphide. Suitable sulphides are alkali metal sulphides and alkaline earth metal sulphides. Sodium sulphide is preferred. The conversion of compound IVa to compound V conveniently is carried out in dimethyl formamide or hexamethylenephosphoric acid triamide as the solvent. The sulphide preferably is added at room temperature (about 23° C.) and the resulting mixture is heated to about 100° C. giving a crude mixture of biotin ester V.

After distillation of the solvent, the crude mixture of biotin ester V can be subjected directly to hydrolysis which yields biotin Va. The hydrolysis is carried out in any conventional manner. A suitable method includes treatment of crude mixture V with an alkali metal hydroxide (e.g., sodium hydroxide). Conventional temperature ranges for hydrolysis are utilized.

If desired, compounds IV, IVa, V and Va can be resolved into their stereoisomers by conventional resolution techniques.

In accordance with another aspect of the invention, compound I, used as a starting material in Reaction Scheme 1, is prepared from 2H-chromene of the formula:

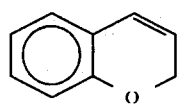

VI by the following reaction scheme:

REACTION SCHEME 2

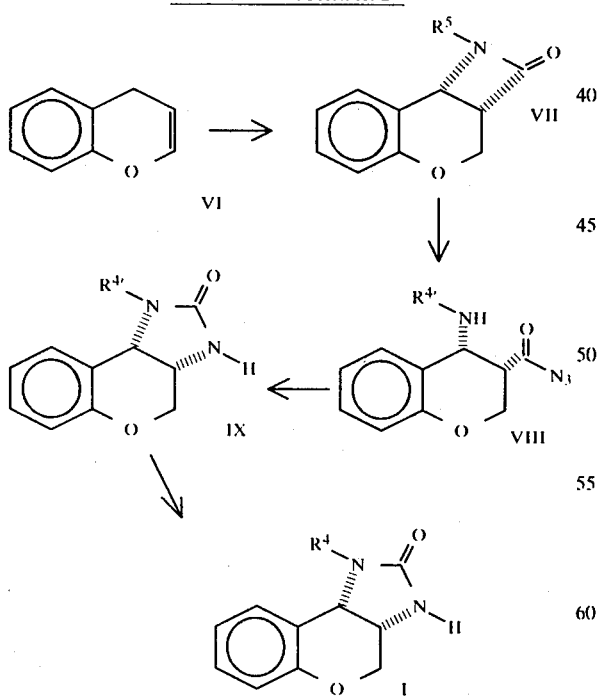

wherein $R^4$ is hydrogen; $R^{4'}$ is —$SO_2N_3$; and $R^5$ is —$SO_2Cl$.

In accordance with Reaction Scheme 2, 2H-chromene of formula VI is reacted with chlorosulphonylisocyanate to give compound VII wherein $R^5$ is —$SO_2Cl$.

This reaction is preferably carried out in an inert organic solvent (e.g., a chlorinated hydrocarbon such as methylene chloride or chloroform, or an ether such as tetrahydrofuran).

The reaction is initially carried out at the lowest temperatures possible, namely at temperatures between −60° C. and −35° C. The resulting reaction mixture is left to stand (for example, for 3 hours at −60° C.), then within 4 hours is allowed to warm to −35° C. and subsequently is left overnight at this temperature. There is obtained compound VII wherein $R^5$ is —$SO_2Cl$.

Compound VII is converted into compound VIII wherein $R^{4'}$ is azidosulphonyl (i.e., —$SO_2N_3$), in a sodium azide/triethylammonium azide/hydrazoic acid system: The reaction preferably proceeds in an inert organic solvent (e.g., a halogenated hydrocarbon such as methylene chloride or chloroform) and at low temperatures. Preferred temperatures are about −10° C., to about −20° C.

Compound VIII is converted into compound IX by a Curtius degradation. That is, compound VIII is heated in an organic solvent (e.g., toluene or benzene) at about 60°–100° C., preferably at about 80° C. to yield compound IX.

Compound IX, wherein $R^{4'}$ is —$SO_2N_3$, can be converted into compound I, wherein $R^4$ is hydrogen, by cleavage of the azidosulphonyl group of compound IX.

The cleavage of the azidosulphonyl group can be carried out by any conventional cleaving method. For example, compound IX can be heated to boiling in the presence of an alkali metal sulphite (e.g., sodium sulphite) in aqueous solution. Alternatively, hydrogen sulphide can also be used in place of the alkali metal sulphite.

Compounds I and IX can be collectively represented as a compound of the formula:

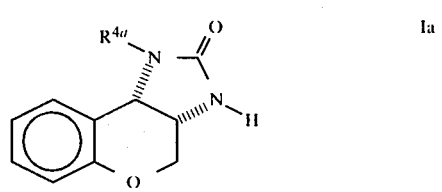

Ia wherein $R^{4a}$ is hydrogen or azidosulphonyl.

In accordance with a further aspect of the invention, compound VII wherein $R^5$ is —$SO_2Cl$ can be converted to a corresponding compound wherein $R^5$ is hydrogen. The conversion occurs by reductive removal of the chlorosulphonyl group of compound VII using sodium iodide and sodium bicarbonate.

The following Examples further illustrate the invention. All temperatures are in degrees Centigrade, unless otherwise stated. Room temperature is approximately 23° C. Ether connotes diethyl ether. Petroleum ether connotes the mixture of hydrocarbons of the methane series, principally pentanes and hexanes boiling between about 35° and 80° C.

EXAMPLE 1

5.71 g of 3a,9b-cis-1,2,3,3a,4,9b-hexahydrochromeno[3,4-d]imidazol-2-one and 1.38 g of lithium amide are suspended in 45 ml of ethylamine in a 200 ml round flask. The round flask is attached via a head to a condenser which is cooled to −50° C. by means of a cryostat.

The apparatus is flushed with nitrogen (dried over potassium hydroxide) and the suspension is stirred magnetically under reflux for 4 hours. 1.67 g of 3 mm lithium wire (rinsed for a short time with nitrogen) are added through the head and the mixture is stirred for 10 minutes. There are then added, at intervals of 10 minutes under nitrogen and without interrupting the stirring, 10 ml, 10 ml, 30 ml and 30 ml portions of dimethylamine. The mixture is stirred for 14 hours and then, in order to decolourise the deep blue mixture and in order to remove unreacted lithium, filtered through a filter packed with glass wool. After removal of the amine (nitrogen atmosphere), the yellowish residue is treated with 100 g of ice and stirred for 0.5 hour. After filtration of the precipitated product, concentration and saturation of the mother liquor with ammonium sulphate and renewed filtration, the entire material on the filter is washed three times with 10 ml of cold water, dried and recrystallized from 200 ml of methanol. After concentration of the mother liquor and drying (24 hours at 80° C. and 0.01 mm), there are obtained 3.7 g of 3a,9b-cis-1,2,3,3a,4,6,7,8,9,9b-decahydro-chromeno[3,4-d]-imidazol-2-one of melting point 257°–260° C.

EXAMPLE 2

3.94 g of the decahydro compound of Example 1 are suspended in 70 ml of water, 3 ml of acetonitrile and 5 ml of ether in a 250 ml round flask. 4.1 g of m-chloroperbenzoic acid in 50 ml of ether are slowly added dropwise (during 2 hours) to the resulting suspension at room temperature with vigorous stirring. After completion of the addition, the phases are separated in a separating funnel, the aqueous phase is extracted three times with 30 ml of ether, the combined ether phases are extracted once with 5 ml of water and the aqueous phase is subsequently freed from solvent residues on a rotary evaporator. This aqueous solution is cooled to 0° C. and added to an ice-cold solution of 4.33 g of sodium periodate in 40 ml of water. The mixture is left to stand at 0° C. for 2 hours, warmed to room temperature and held at this temperature for 2 hours. After filtering off the crystallized-out product, the filtrate is concentrated to 40 ml. After renewed filtration, the entire product is recrystallised from water. Including the product obtained after concentration of the mother liquor, there are obtained, after drying over phosphorus pentoxide (10 hours at 60° C. and 0.01 mm), 3.65 g of 1,10-cis-3-oxa-11,13-diazabicyclo[8.3.0]tridecane-4,9,12-trione of melting point 215°–230° C. (decomposition).

EXAMPLE 3

1 g of finely powdered 1,10-cis-3-oxa-11,13-diazabicyclo[8.3.0]tridecane-4,9,12-trione is stirred at room temperature for 2 hours in 60 ml of absolute methanol with 0.24 g of sodium borohydride in the presence of 0.7 g of molecular sieve 3 Å and then the mixture is left to stand for 7 hours. After filtration the pH value of the solution is brought to 4.7 with glacial acetic acid and the solvent is distilled off. The residue is treated three times with 15 ml of absolute methanol each time and the methanol is in each case evaporated off and subsequently the residue is treated with 20 ml of absolute methanol. After distillation of the methanol at normal pressure, solvent remains are removed on a rotary evaporator. The residue is treated with 5 ml of saturated ammonium sulphate solution, crystallization occurring. The product obtained is filtered off, dried and recrystallised from a small amount of methanol. There is obtained 0.73 g of a mixture of ($\epsilon$R,4S,5S) and ($\epsilon$S,4R,5R)-5-hydroxymethyl-2-oxo-$\epsilon$-hydroxy-4-imidazolidinecaproic acid methyl ester of melting point 165°–167° C. (from methanol).

EXAMPLE 4

0.3 g of the crude mixture of Example 3 is dissolved in 5 ml of absoute pyridine and the solution is cooled to −10° C. 1.32 g of methanesulphonic acid chloride are added dropwise to the solution while stirring and with exclusion of moisture, the temperature is held at −10° C. for a further 10 minutes and subsequently the mixture is stirred at room temperature for a further 2 hours. The majority of the pyridine is then distilled off at room temperature under a pressure of 0.05 mm and the residue is triturated with 10 ml of petroleum ether (boiling point 40°–50° C.). The petroleum ether phase is decanted off and the residue is freed from petroleum ether remains at a pressure of 0.05 mm. After the addition of 5 g of ice, the mixture is extracted three times with 10 ml of methylene chloride. After washing with three 3 ml portions of 2 N hydrochloric acid and with one 5 ml portion of ice-water, the combined methylene chloride extracts are dried over sodium sulphate. After filtration, the methylene chloride is distilled off on a rotary evaporator and the residue, ($\epsilon$R,4S,5S)-and ($\epsilon$S,4R,5R)-5-methylsulphonyloxymethyl-2-oxo-$\epsilon$-methylsulphonyloxy-4-methazolidinecaproic acid methyl ester, is dried at reduced pressure under room temperature.

EXAMPLE 5

The crude mixture of ($\epsilon$R,4S,5S)- and ($\epsilon$S,4R,5R)-5-methylsulphonyloxymethyl-2-oxo-$\epsilon$-methylsulphonyloxy-4-methazolidinecaproic acid methyl ester (0.34 g) obtained according to Example 4 is dissolved in 5 ml of hexamethylenephosphoric acid triamide and the solution is de-gassed with nitrogen. 0.21 g of sodim sulphide ($Na_2S.9H_2O$) are added to the solution at room temperature while stirring and the resulting solution is heated to 100° C. within 30 minutes under nitrogen. After stirring at 100° C. for 2 hours, the majority of the hexamethylenephosphoric acid triamide is distilled off on a water-bath at 0.01 mm. The yellow residue is triturated with 20 ml of petroleum ether (boiling point 40°–50° C.) and the petroleum ether phase is decanted off. After the removal of petroleum ether residues on a rotary evaporator, the residue is taken up in 100 ml of 2 N sodium hydroxide, treated with 0.2 g of active carbon and heated on a boiling water-bath for 3 hours. The hot solution is filtered, the filtrate is brought to a pH value of 3 with concentrated hydrochloric acid, concentrated to 3 ml and cooled at 0° C. for 30 minutes. The supernatant solution is decanted off from the precipitated product and the latter is again heated under reflux for 15 minutes with 10 ml of water and 0.1 g of active carbon. After filtration, the filtrate is concentrated to 3 ml and cooled in an ice-bath for 1 hour. The thus-obtained flocculent, yellowish product is filtered off, pressed dry and taken up in 3 ml of boiling methanol. After trituration and filtration, the thus-obtained almost colourless product is recrystallised from a small amount of water. After drying over phosphorus pentoxide (at 80° C. and 0.05 mm for 14 hours), there are obtained colourless, needle-like crystals of (±) biotin of melting point 236°–237° C.

The methyl ether of this compound melts at 132°–134° C.

The reduction of 3a,9b-cis-1,2,3,3a,4,9b-hexahydro-chromeno[3,4-d]imidazol-2-one to give 3a,9b-cis-1,2,3,3a,4,6,7,8,9,9b-decahydro-chromeno[3,4-d]imidazol-2-one can be carried out, instead of in one-step as described in Example 1, but also in two-steps, the corresponding octahydro compound being obtained in the first step. This two-step reduction can be carried out as described in Examples 6 and 7.

EXAMPLE 6

A suspension of 2 g of 3a,9b-cis-1,2,3,3a,4,9b-hexahydro-chromeno[3,4-d]imidazol-2-one in 150 ml of liquid ammonia is treated with 6 g of potassium tert.butoxide and the mixture is stirred for 0.5 hour. After the addition of 30 ml of tert.butanol, there is gradually introduced over a period of 60 minutes 0.8 g of lithium which has been cut into 25 mg portions. The addition of the lithium should be carried out at such a rate that, during the entire reaction period, the mixture is blue in colour. After completion of the addition of the lithium and as soon as the blue colour of the mixture has disappeared, 150 ml of absolute methanol are added in order to decompose the tert.butoxide present. After distillation of the ammonia, 100 g of ice are added to the methanolic residue and the methanol is distilled off completely on a rotary evaporator. The product precipitating from the solution (cooled to 0° C.) is, after filtration, washed three times on the filter with 25 ml of ice-water. After drying, the crude product is recrystallised from a small amount of acetonitrile containing 0.25 g of maleic acid anhydride. After drying (14 hours at 25° C. and 0.01 mm), there are obtained 1.4 g of 3a,9b-cis-1,2,3,3a,4,6,9,9b-octahydro-chromeno[3,2-d]-imidazol-2-one of melting point 253°–255° C. (from methanol).

EXAMPLE 7

0.1 g of 3a,9b-cis-1,2,3,3a,4,6,9,9b-octahydro-chromeno[3,2-d]-imidazol-2-one dissolved in 22 ml. of absolute methanol, is added at 20° C. in a hydrogen atmosphere (770 mmHg) to 20 mg of platinum oxide in 5 ml. of absolute methanol. The mixture is stirred and the calculated amount of hydrogen is taken up within 10 minutes. After 15 minutes, the hydrogenation is interrupted, the catalyst is filtered off and the solvent is removed on a rotary evaporator. The crystalline residue, 3a,9b-cis-1,2,3,3a,4,6,9,9b-decahydro-chromeno[3,2-d]-imidazol-2-one, melts at 250°–253° C.

The 3a,9b-cis-1,2,3,3a,4,9b-hexahydro-chromeno[3,4-d]imidazol-2-one used as the starting material in Examples 1 and 6 can be prepared as described in following Examples 8–11.

EXAMPLE 8

14.2 g of chlorosulphonylisocyanate are cooled with liquid nitrogen in a 100 ml round flask (fitted with a drying tube charged with calcium chloride and phosphorus pentoxide) until the chlorosulphonylisocyanate solidifies. 13.1 g of 2H-chromene and 6.5 ml of absolute ether are then rapidly added, a light red colouration occurring. The mixture is then immediately cooled with liquid nitrogen for 10 minutes. Subsequently, the vessel is left to stand at −60° C. for 3 hours, then warmed within 4 hours to −35° C. and left to stand at −35° C. overnight (16 hours). The mixture is then warmed to −25° C. for 4 hours and again cooled to −35° C., the flask content solidifying to a light yellowish-red coloured crystal mass which consists of crude 1-chlorosulphonyl-2,3,4,10-tetrahydro-1H-chromeno[3,4-c]azet-2-one.(N-chlorosulphonyl-$\beta$-lactam).

From 1-chlorosulphonyl-2,3,4,10-tetrahydro-1H-chromeno[3,4-c]azet-2-one, there can be obtained by reductive removal of the chlorosulphonyl group using sodium iodide and sodium bicarbonate the compound of formula VII in which $R^5$ is hydrogen. The latter compound melts at 196°–197.5° C. (from chloroform).

EXAMPLE 9

For the further reduction of N-chlorosulphonyl-$\beta$-lactam of Example 8 there is required a buffer system which is prepared as follows:

To a suspension, prepared while stirring, of 27.3 g of sodium azide, 27.6 g of water and 80 ml of methylene chloride are slowly added dropwise, after cooling to 0° C., 20.58 g of concentrated sulphuric acid so that the temperature does not rise above +10° C. After completion of the addition, the mixture is stirred at 0° C. for a further 20 minutes, decanted off from precipitated sodium sulphate and the residue is washed four times with 10 ml of methylene chloride each time. 21.5 g of triethylamine are introduced while stirring into the combined decantates which are dried over sodium sulphate and cooled to −20° C. by external cooling, whereby the internal temperature should not rise above −8° C.

EXAMPLE 10

50 ml of absolute methylene chloride are added to crude 1-chlorosulphonyl-2,3,4,10-tetrahydro-1H-chromeno[3,4-c]azet-2-one (N-chlorosulphonyl-$\beta$-lactam), of Example 8, and as large as possible amount of the lactam is dissolved at −10° C. The thus-obtained solution is added dropwise to the buffer system, of Example 9 held at −20° C. so that the temperature remains between −18° C. and −16° C. After completion of the addition, 30 ml of methylene chloride are added to the still undissolved lactam, this is dissolved at 0° C. and the solution obtained is again added dropwise to the buffer system. After completion of the addition, the mixture is warmed to room temperature within 30 minutes while stirring and then treated with 100 ml of ice-water. The pH value of the aqueous phase is brought to 3.5 with concentrated hydrochloric acid with vigorous stirring. After separation of the phases, the methylene chloride phase is washed three times with 50 ml of cold water. After drying over sodium sulphate and filtration, the methylene chloride is distilled off at room temperature on a rotary evaporator. The thus-obtained bis-azide of formula VIII in which $R^4$ represents the azidosulphonic group is a yellowish, semicrystalline to oily substance. It is taken up in 200 ml of absolute toluene and heated at 85° C. on a water-bath. Nitrogen evolution occurs and, after a short time, a voluminous needle-like precipitate begins to separate out. It is thereupon heated for a further 15 minutes while shaking on a boiling water-bath, subsequently cooled to room temperature and left to stand for 0.5 hour. The precipitate is filtered off and washed on the filter four times with 10 ml of ice-cold methanol. After drying (3 hours at 60° C. and 0.1 mm), there are obtained 16.5 g of 3a,9b-cis-1-azidosulphonyl-1,2,3,3a,4,9b-hexahydro-chromeno[3,4-d]imidazol-2-one in the form of colourless needles of melting point 195° C. After recrystallisation from methanol, the compound melts at 191°–192° C.

EXAMPLE 11

27.2 g of the azidosulphonyl compound of Example 10, 23.2 g of sodium sulphite and 500 ml of water are boiled under reflux in a 4 liter flask for 35 minutes while shaking. Upon cooling, crystallisation sets in and is completed at 0° C. The precipitate is filtered off and washed with 50 ml of cold water. Further product is obtained by concentrating the mother liquor to 80 ml, analogous crystallisation and washing with water. After drying over phosphorus pentoxide (4 hours at 80° C. and 0.1 mm), there are obtained 17.3 g of 3a,9b-cis 1,2,3,3a,4,9b-hexahydro-chromeno[3,4-d]imidazol-2-one of melting point 265° C. (from water). After recrystallisation from ethanol, the compound melts at 260°–263° C.

I claim:

1. A compound of the formula:

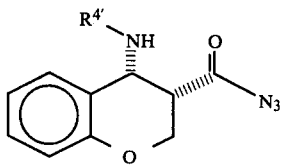

VIII wherein $R^{4'}$ is azidosulphonyl.

* * * * *